(12) United States Patent
Burkett et al.

(10) Patent No.: US 6,582,395 B1
(45) Date of Patent: Jun. 24, 2003

(54) FEEDING TUBE DEVICE AND METHOD

(75) Inventors: Jeffrey S. Burkett, Neenah, WI (US); Raymond F. Georgen, Neenah, WI (US)

(73) Assignee: J & R Medical Devices, Inc., Neenah, WI (US)

( * ) Notice: Subject to any disclaimer, the term of this patent is extended or adjusted under 35 U.S.C. 154(b) by 118 days.

(21) Appl. No.: 09/736,866

(22) Filed: Dec. 14, 2000

(51) Int. Cl.[7] ............................................. A61M 29/00

(52) U.S. Cl. ................................... 604/96.01; 604/910

(58) Field of Search ........................... 604/910, 96.01, 604/539, 284; 606/191–194

(56) References Cited

U.S. PATENT DOCUMENTS

| | | | | |
|---|---|---|---|---|
| 3,633,586 A | * | 1/1972 | Sheridan | 604/910 |
| 3,805,794 A | * | 4/1974 | Schlesinger | 604/96.01 |
| 4,367,740 A | * | 1/1983 | Evanoski, III | 604/910 |
| 4,551,130 A | * | 11/1985 | Herbert et al. | 604/247 |
| 4,601,701 A | * | 7/1986 | Mueller et al. | 604/83 |
| 4,701,159 A | * | 10/1987 | Brown et al. | 604/43 |
| 4,796,615 A | * | 1/1989 | Bullock et al. | 604/532 |
| 5,391,159 A | * | 2/1995 | Hirsch et al. | 604/268 |
| 5,458,583 A | * | 10/1995 | McNeely et al. | 604/96.01 |
| 6,010,479 A | | 1/2000 | Dimitri | |

OTHER PUBLICATIONS

Caulfield, *Percutaneous Endoscopic Gastrostomy Placement in Children*, Pediatric Endoscopy, vol. 4, No. 1, Jan. 1994, pp. 179–193.

Davidson, et al., *Technique and Complications of Percutaneous Endoscopic Gastrostomy in Children*, Aust. N.Z. J. Surg, 65, pp. 194–196 (1995).

Kimber, et al., *Limitations of percutaneous endoscopic gastrostomy in facilitating enteral nutrition in children: Review of the shortcomings of a new technique*, J. Paediatr. Child Heath, 35, pp. 427–431 (1999).

Jarnagin et al., *The Efficacy and Limitations of Percutaneous Endoscopic Gastrostomy*, Arch Surg., vol. 127, Mar. 1992.

Deitel, et al., *Percutaneous Endoscopic Gastrostomy by the "Pull" and "Introducer" Methods*, The Canadian Journal of Surgery, vol. 31, No. 2, Mar. 1988.

Crombleholme et al., *Simplified "Push" Technique for Percutaneous Endoscopic Gastrostomy in Children*, Journal of Pediatric Surgery, vol. 28, No. 10, Oct. 1993, pp. 1393–1395.

Gauderer, et al., *Gastrostomy Without Laparotomy: A Percutaneous Endoscopic Technique*, Journal of Pediatric Surgery, vol. 15, No. 6, Dec. 1980, pp. 872 and 874.

Werline, et al., *Early feeding after percutaneous endoscopic gastrostomy is safe in children*, Gastrointestinal Endoscopy, vol. 40, No. 6, 1994, pp. 692–693.

Mollitt, et al., *Complications of Retained Internal Bolster After Pediatric Percutaneous Endoscopic Gastrstomy*, Journal of Pediatric Surgery, vol. 33, No. 2, Feb. 1998, pp. 271–273.

(List continued on next page.)

*Primary Examiner*—Sharon Kennedy
(74) *Attorney, Agent, or Firm*—Boyle Fredrickson Newholm Stein & Gratz S.C.

(57) ABSTRACT

A feeding tube medical apparatus having a catheter head and catheter that allows easy insertion and removal of the catheter within a patient needing enteral feeding. The invention also relates to a method for easy insertion and removal of the catheter. The catheter has a slim profile, a balloon bolster, and a tapered guide tube that promote easy insertion of the catheter down a patient's mouth and into his or her stomach. In addition, the catheter head, containing ports for feeding, medicating, and filling the balloon bolster, is removably connected to the catheter so that it need not be inserted through the patient along with the catheter.

20 Claims, 5 Drawing Sheets

OTHER PUBLICATIONS

Khattak, et al., *Percutaneous Endoscopic Gastrostomy in Pediatric Practice: Complications and Outcome*, Journal of Pediatric Surgery, vol. 33, No. 1, Jan. 1998, pp. 67–72.

Quintão, et al., *Improvement of children's nutritional status after enteral feeding by PEG: an interim report*, Gastrointesinal Endoscopy, vol. 50, No. 2, 1999, pp. 183–188.

Grief, et al., *Fatal necrotizing fascitis complicating percutaneous endoscopic gastrostomy*, Gastrointestinal Endoscopy, vol. 32, No. 4, 1986, pp. 292–294.

American Gastroenterological Association, *American Gastroenterological Association Medical Position Statement: Guidelines for the Use of Enteral Nutrition*, http://www.wbsaunders.com/gastro/policy.

ASGE: Procedure Manual, http://www.asge.org/resources/maual.

Role of Percutaneous Endoscopc Gastrostomy, A SAGES Co–Endorsed ASGE Guideline for Clinical Application, http://www.sages.org.

Cook Diagnostic & Interventional Products, *Gastroenterology*, http://www.cookincorporated.com.

Mill–Rose Labroatories, Inc., Instruments for Endoscopy, http://www.mrlabsinc.com.

Bard Interventional Products Division, *Gastrostomy Feeding Devices*, http://www.bardinterventional.com.

Applied Medical Technology—Product Info—G–Tube, http://www.appliedmedical.net.

Abbott Laboratories, Ross Product Division, *Enteral Feeding Devices, Tubes*, http://www.ross.com.

\* cited by examiner

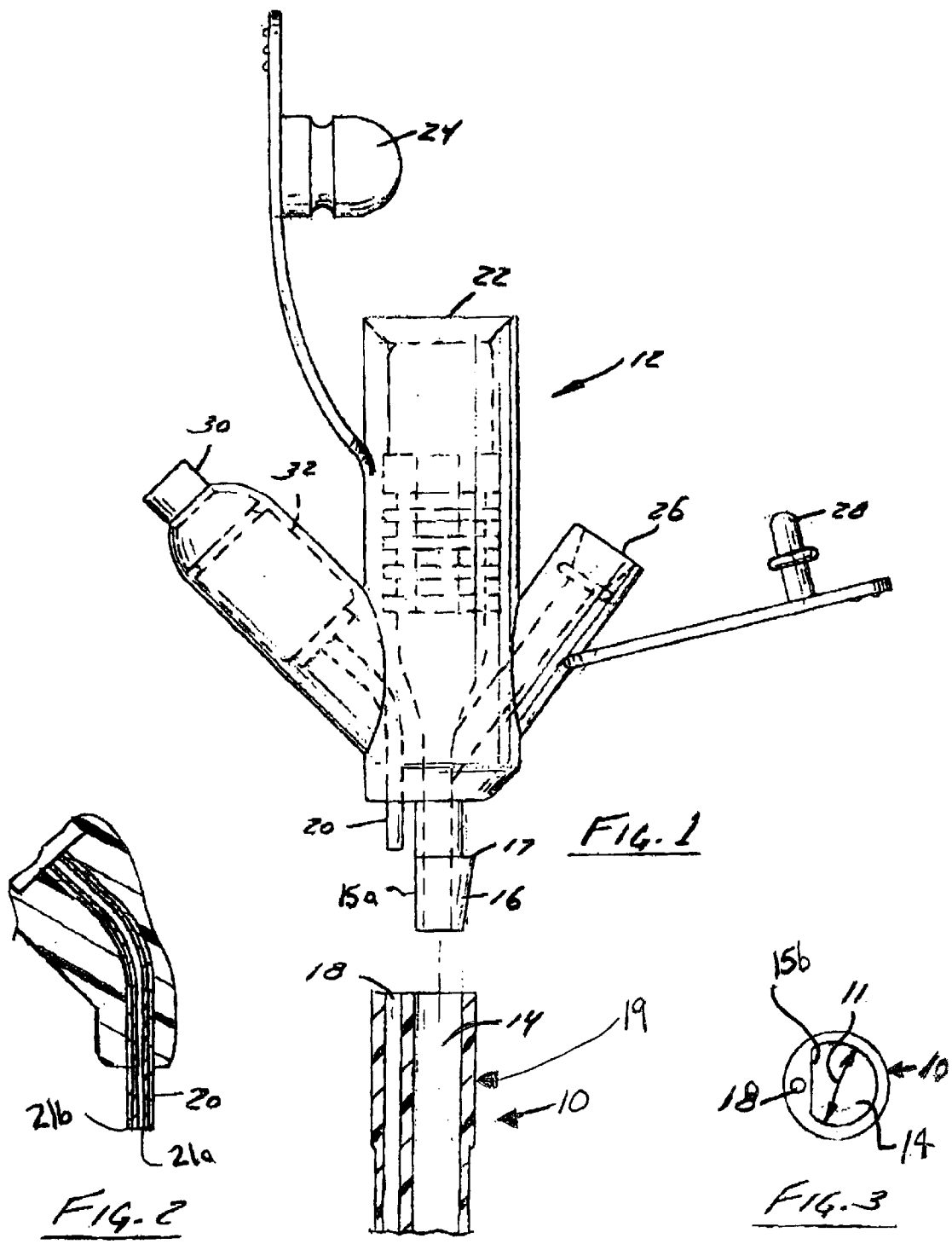

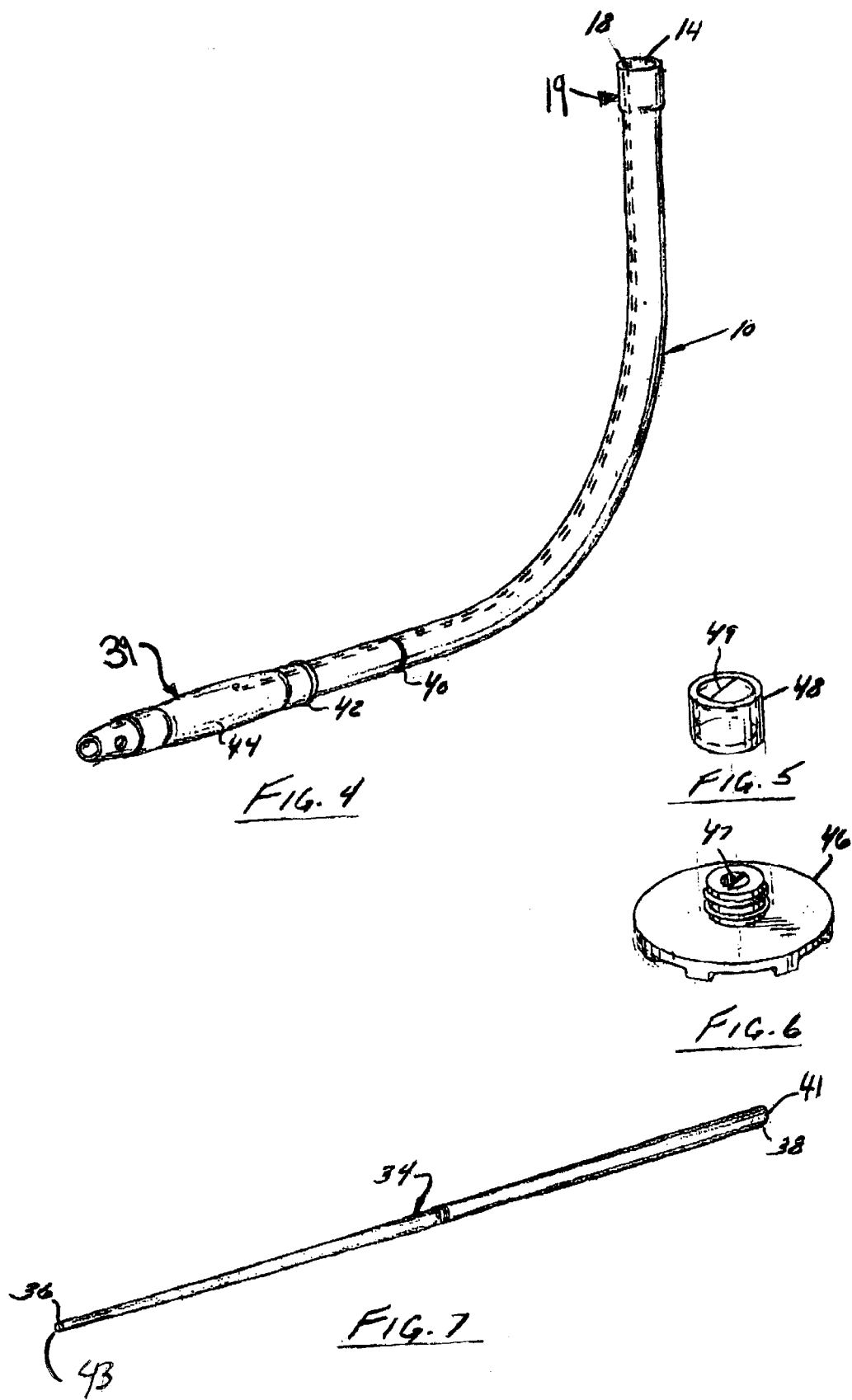

FEEDING TUBE DEVICE AND METHOD

BACKGROUND OF THE INVENTION

1. Field of the Invention

The present invention relates generally to a device and method for placing a tube for tube feeding a patient. Specifically, the invention relates to a novel tube feeding device that separates and thus allows insertion and removal by an advantageous combination of techniques.

2. Discussion of Related Art

Tube feeding is necessary when a patient requires long-term feeding assistance. In tube feeding placements, an incision is made through a patient's abdominal wall and stomach and a catheter is inserted therein. The patient is then fed a nutrient solution directly through the catheter into the stomach. However, methods for placing the catheter vary, as do the catheter specifications and techniques for removing the catheters.

Current methods for insertion of a percutaneously placed catheter include a pull-through technique, a push technique, and an introducer technique. Both the pull-through and the push technique require a catheter to be passed through the mouth, down the esophagus, through the stomach, and out the incision. The passage of the catheter in this manner can cause damage to the back of the throat and esophagus, especially when the catheter includes an apparatus at its leading and trailing ends for use in feeding and in holding the catheter in place. In addition, when a retention apparatus is included, removal of the device must usually be accomplished with a second endoscopy. Both of these disadvantages are particularly problematic in neonates, who have smaller less well-developed passageways and are thus more prone to injury from tube placement. Moreover, neonates often require potentially risky general anesthetic for each endoscopy. Another method of inserting a catheter, the introducer technique, avoids these problems by pushing the catheter directly into the patient's incision. A dilating sheath must first be inserted though the incision, then the catheter is inserted by pushing it through the sheath. The sheath is then removed and the catheter is fixed in place. In this technique, endoscopy is not required for removal since an inflatable (Foley) bolster is used. It can be deflated and the entire catheter removed with a gentle pull. However, the incision made in an introduction insertion must be larger than in the other techniques, and the larger incision in the abdominal wall and stomach creates a higher likelihood of leaking around the area of the catheter.

It would therefore be desirable to have a device which would enable the passage of a catheter without damaging the back of the patient's mouth and esophagus, would not require an unacceptably large incision in the patient's abdominal wall, and would not require repeat endoscopy for removal.

SUMMARY OF THE INVENTION

The present invention provides a device and a method which may be used for tube feeding procedures such as percutaneous endoscopic gastrostomy (PEG). The device allows easy passage of a catheter through a patient, does not require an excessively large incision, and does not require repeat endoscopy for removal.

The device of the present invention allows easy passage by providing a catheter with a tapered insertion portion and an inflatable internal bolster, and also providing a separate catheter head. The slim profile of the device allows easier insertion into a patient, even a neonatal patient whose esophagus is small, than any existing device, while still providing the required internal bolster and feeding port.

The device of the present invention thus enables a physician to use the push technique to insert a catheter without fear of damaging the patient. After placing the catheter, the physician can inflate the bolster and remove the tapered insertion portion, then attach the catheter head to the catheter for feeding.

Because the push technique of insertion is enabled without the risks of damage previously encountered, the incision need not be any larger than necessary to allow the passage of the catheter. Moreover, because the slim profile that eases passage of the catheter includes an inflatable internal bolster, removal of the device does not require repeat endoscopy.

These, and other, aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which:

FIG. 1 is a side view of a catheter head and a cutaway view of a connecting double lumen catheter having a large lumen and a small lumen;

FIG. 2 is a partial cutaway view of the catheter head showing a small lumen fitting;

FIG. 3 is a cross-sectional view of the catheter;

FIG. 4 is a perspective view of the catheter;

FIG. 5 is a perspective view of the seal sleeve which fits over the catheter;

FIG. 6 is a perspective view of a flange;

FIG. 7 is a perspective view of a guide tube;

Figure 8:
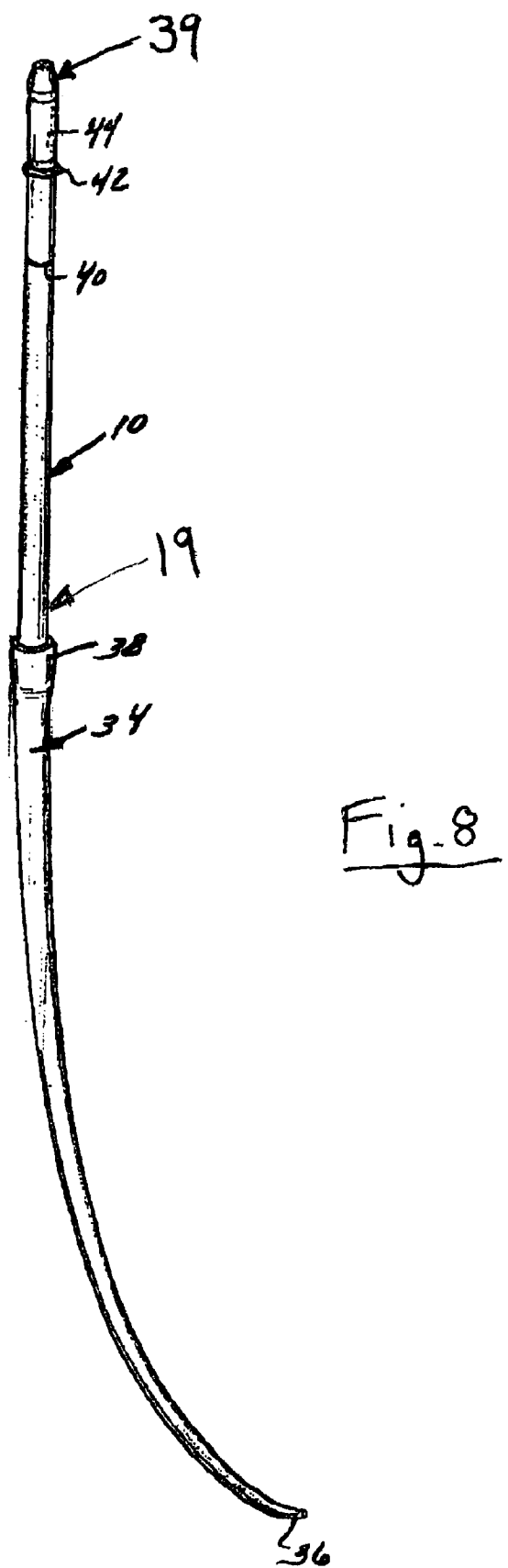
FIG. 8 is side view of the guide tube and the connected double-lumen catheter.

In describing the preferred embodiment of the invention which is illustrated in the drawings, specific terminology will be resorted to for the sake of clarity. However, it is not intended that the invention be limited to the specific terms so selected and it is to be understood that each specific term

DETAILED DESCRIPTION OF THE PREFERRED EMBODIMENT

1. Resume

The present invention is a medical apparatus consisting primarily of an catheter head, a catheter, and a tube. In the preferred embodiment, the catheter head has at least two fittings that allow the catheter head to connect with two channels, or lumens, that are contained within the catheter. The catheter has a large lumen for feeding and a small lumen for gas, such as air, or fluid. The catheter has a balloon at its distal end, which is filled by way of the smaller lumen. The catheter also has a somewhat rigid guide tube attached near its top end, and the proximal end of the guide tube itself is tapered. The tapered guide tube is slightly larger than the catheter at the point where the two parts meet, and can be removed from the catheter, possibly by cutting it off.

The catheter head has preferably three ports, one for food, one for medicine, and one for filling the balloon. The food and medicine ports meet within the catheter head and terminate at the large-lumen fitting. The food and medicine ports have caps for when they are not being used. The third port, the one for filling the balloon, contains a valve and terminates in a metal tube that serves as the small-lumen fitting. The large and small lumen fittings are designed to form a friction fit within the lumens of the catheter. The large-lumen fitting has a frusto-conical shape, and the small-lumen fitting is coated for secure connection within the lumens of the catheter.

The catheter of this invention, besides having a large and a small lumen within, also has a position mark and a ridge toward its bottom end. In addition, a flange and/or a seal sleeve are provided to pass over the catheter.

A preferred method of this invention is the insertion of a feeding tube by the push method, as is well known in the art, using an inventive slim profile catheter and guide tube assembly that features a removable head. The invention disclosed herein allows the physician to perform the catheter (feeding tube) insertion, remove and discard the guide tube, and connect the head to the catheter. This way the potential damage caused by forcing too much down a patient's throat is minimized. Finally, when the patient no longer needs the catheter in place, or needs a replacement catheter, it can be removed by deflating the bolster ballon and simply pulling rather than by a repeat endoscopy.

2. Overview

Referring generally to the drawings FIGS. 1–11, this invention pertains to a medical apparatus 3 including a feeding tube device 5. An advantageous method for inserting the apparatus 3 into a patient's stomach is also revealed.

Referring to FIG. 1, the gastrostomy tube or feeding tube device 5 preferably includes a double-lumen catheter 10 and a catheter head 12. The lumens, or channels 14, 18 of the catheter 10 correspond with lumen fittings of the catheter head 12. Accordingly, the large lumen 14 of the catheter 10 can accept the large-lumen fitting 16 of the catheter head 12 and the small lumen 18 of the catheter can accept the small-lumen fitting 20 of the catheter head 12.

The catheter head 12 is generally Y-shaped and also features a feeding port 22 and feeding port cap 24, a medication port 26 and medication port cap 28, and a balloon-filling port 30 containing a valve 32. The feeding port 22 and medication port are in fluid communication with the large lumen 14 when the large-lumen fitting 16, which may be generally frusto-conical, is inserted into the large lumen 14. The frusto-conical shape gives the large-lumen fitting 16 a raised outer lip 17 for a tighter fit when connected to the large lumen 14. The balloon-filling port 30 is in fluid communication with the small lumen 18 via the valve 32 when the small-lumen fitting 20 is inserted into the small lumen 18.

Preferably, as best shown in FIG. 2, the small lumen 20 includes a smaller, metal, inner rod 21a to prevent the tube from collapsing and an outer coating 21b (preferably comprised of silicone) over the inner metal rod 21a to protect it and add a friction producing surface for better securing to the small lument 18.

Referring now to FIG. 3, the double-lumen catheter 10 is shown in cross-section to better contrast the size of the large lumen 14 and the small lumen 18. The diameter 11 of the large lumen 14 is in some places nearly equal to the diameter of the catheter as shown. In one preferred embodiment, the large-lumen fitting 16 of the catheter head 12 has a flat edge 15a (see FIG. 1) for interconnection with a flat surface 15b of the large lumen 14 of the catheter 10 (see FIG. 3).

FIG. 4 shows the catheter 10. Preferably, the catheter 10 also features a position mark 40, a ridge 42, and a balloon-type bolster 44, sometimes known as a Foley balloon. The diameter of the catheter may slightly increase at a top portion 19 as shown.

FIG. 5 shows a sleeve 48 having a center opening or inner hole 49 for tightly receiving the top portion 19 of the catheter 10 (See FIG. 4). The sleeve 48 serves to tightly secure the catheter 10 to the catheter head (not shown). In the preferred embodiment, the seal sleeve 48 is a 2 cm length of silicone tubing with an inner diameter 49 just larger than the diameter 11 of the catheter 10.

In addition, the preferred embodiment includes a flange 46 and a seal sleeve 48 as shown in FIG. 6. The flange 46 has an inner diameter 47 just larger than the diameter 11 of the catheter 10 so that it may be passed over the catheter 10 but will not slip off.

FIG. 7 illustrates a guide tube 34. In the preferred embodiment, the guide tube 34 has a tapered proximal end 36 and a distal end 38 to make traveling through the body less difficult. Thus, the distal end 38 has a diameter 43 which is larger than the diameter 41 of the proximal end 36. The diameter of the distal end 38 may be smaller than the diameter 11 of the catheter 10 for ease of fit.

FIG. 8 shows the top portion 19 of the catheter 10 connected to the distal end 38 of the guide tube.

In one of the preferred embodiments, the catheter 10 and most of the catheter head 12 may be constructed of medical grade silicone. However, the device 5 could also be made of polyurethane or any material appropriate for medical use. The small-lumen fitting 20 of the catheter head 12, however, should preferably be made of metal but may be made of any rigid material so that the fitting 20 can be inserted without crumpling and, when inserted, will not collapse within the small lumen 18. If the small-lumen fitting 20 is constructed of a metal, it preferably is bonded with a plastic coating or another appropriate material to increase its surface friction.

The invention disclosed is particularly valuable for use in neonates, who are least equipped to handle the placement and removal of previously known feeding tubes. The components of one of the preferred embodiments are thus sized for neonatal use, but obviously can be differently sized for larger children or for adults without departing from the invention. For example, in one preferred embodiment, the diameter 11 of the catheter 10 is 14 or 16 french and between 15 and 20 cm in length, the position mark 40 is located 2 cm from the proximal edge of the balloon 44, and the ridge 42 is 2 mm larger than the diameter 11 of the catheter 10. However, these dimensions are given to describe the preferred embodiment rather than to limit the scope of the invention.

The method of the present invention includes procedures well known in the art of feeding tube insertion. For instance, it is well known that a feeding tube insertion begins by insufflating a patient's stomach 52 and using an endoscope (not shown) to illuminate an area where the stomach 52 has been pressed against the anterior abdominal wall 54. What is not known in the art is best illustrated in FIG. 10.

Figure 10:
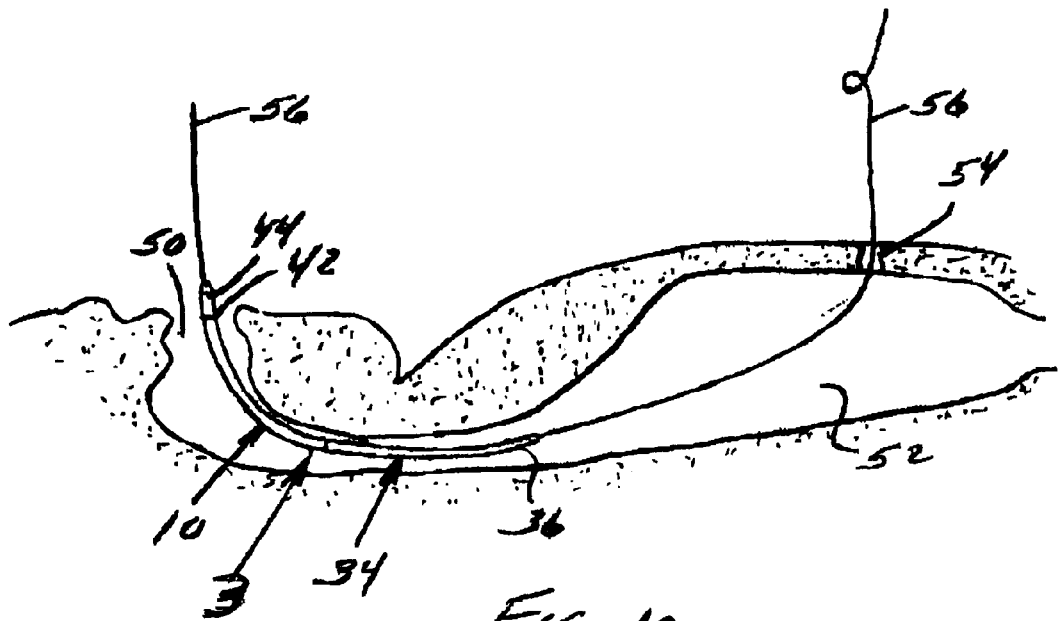
FIG. 10 is a schematic illustrating a guidewire extending down a patient's throat, through the stomach and out a side wall and the insertion of the catheter and connected guide tube along the same.

In FIG. 10, as is known in the art, a physician (not shown) pushes a portion of the medical apparatus 3 including the guide tube 34 and catheter 10 described herein over a guidewire 56, tapered proximal end 36 of the guide tube 34 first. The tapered end 36 of the guide tube 34 continues to follow the guidewire 56 out the anterior abdominal wall 54. When the tapered end 36 is visualized outside the abdominal wall 54, it is pulled with an even gentle traction until the position mark 40 of the catheter 10 is visualized. In the preferred embodiment, the ridge 42 abuts the wall increase the friction slightly and making it more difficult to pull the tube accidentally completely though. As a result, when the tugging becomes slightly more difficult the physician then stops pulling.

Figure 9:
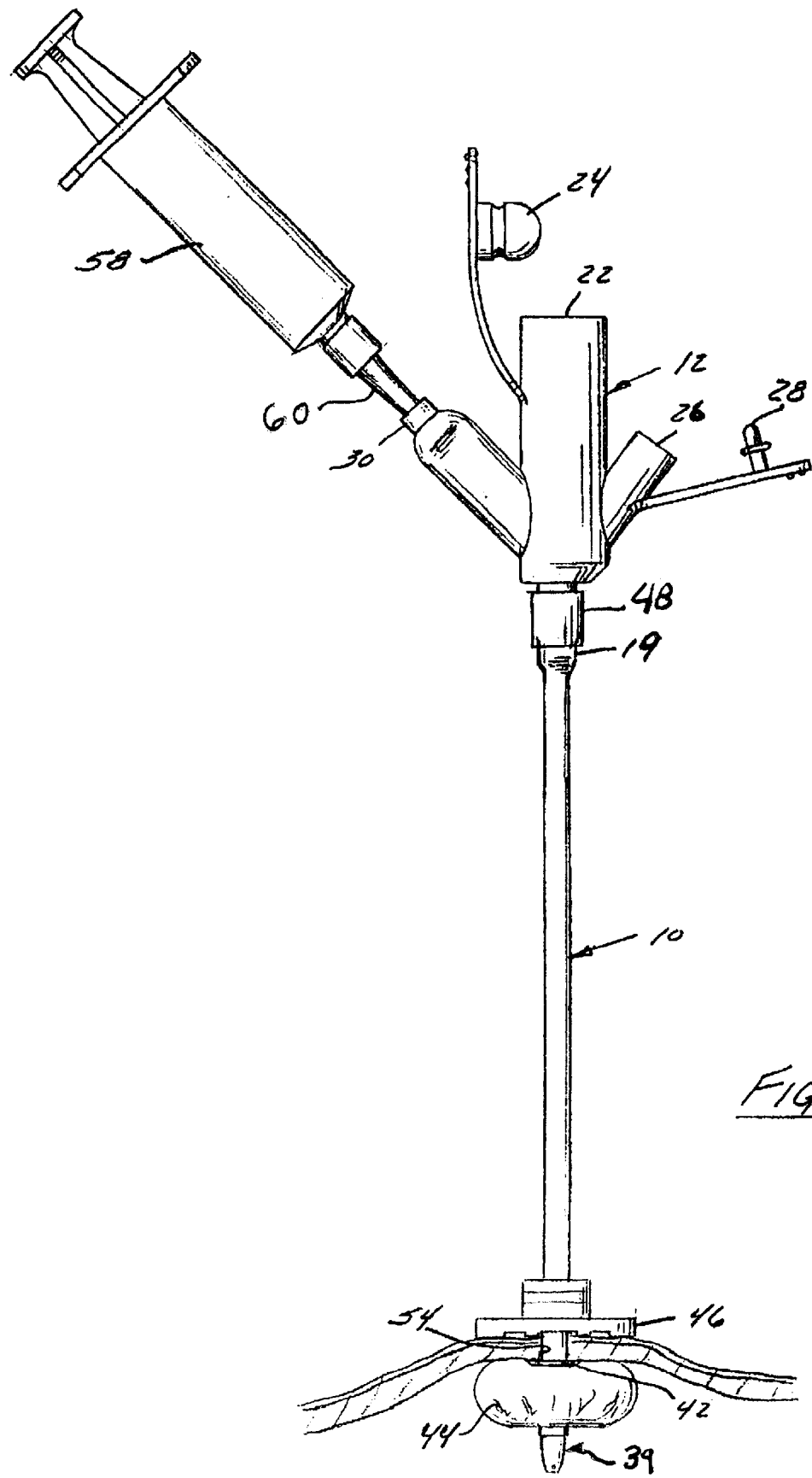
FIG. 9 is a side view of the double-lumen catheter, the catheter head, and a syringe operably engaged to a side wall of a stomach.
Figure 11:
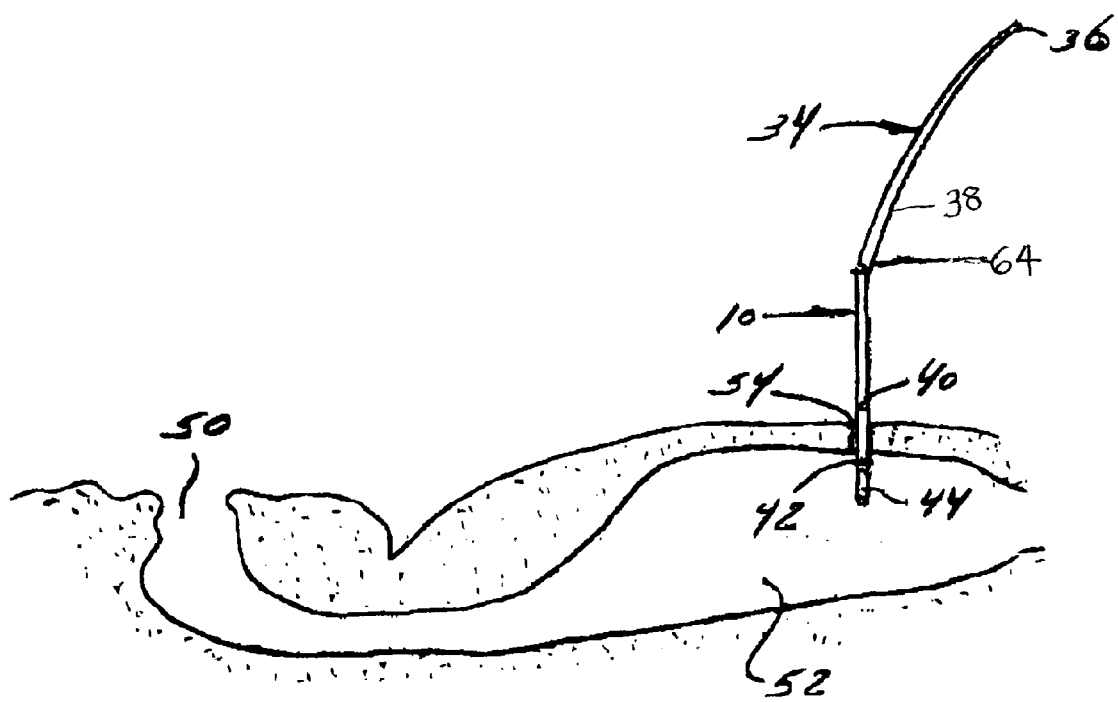
FIG. 11 is a schematic illustrating the catheter and guide tube protruding through the stomach and out a side wall and the guide tube being removed from the catheter.

As illustrated in FIG. 11, the guide tube 34 is then removed along 64 mark, leaving only the catheter 10. FIG. 9 shows the catheter head 12 attaches to the catheter 10 via the fittings 16, 20. Flange 46 fits over the catheter 10 and secured against the abdominal wall 54. The junction between the catheter 10 and catheter head 12 is preferably sealed by sliding the seal sleeve 48 over the connection.

In FIG. 9, a syringe 58 and the tip of the syringe 60 is then inserted into the valve 32 of the balloon-filling port 30, which inflates the balloon 44 inside the patient's stomach 52 with about 5 mm of water. The feeding tube insertion is then complete and feeding of the patient may begin as is known in the art.

When the patient no longer needs enteral feeding, the tip of a syringe 60 is inserted into the valve 32 of the balloon-filling port 30 and the water is withdrawn from the balloon 44 into the syringe 58, causing the balloon 44 to collapse. The catheter 10 can then be removed from the stomach 52 using a gentle pull.

The method of the present invention has been described in terms of the preferred sequence, however, the invention includes all equivalent variations. For instance, it is possible to dispense with the silicone seal tube 48 or fill the balloon 44 with another fluid, such as an appropriate gas, without departing from the invention and the scope of the appending claims.

In is understood that the individual components need not be formed in the disclosed shapes, or assembled in the disclosed configuration, but could be provided in virtually any shape, and assembled in virtually any configuration, so as to provide the same functionality. For example, the term medical apparatus may include a guidewire, a catheter, a guide tube, and a catheter head. Further, although the guide tube described herein is a physically separate module, it will be manifest that the may be integrated into the catheter with which it is associated a removed therefrom by cutting. A mark made be placed on the combined catheter/guide tube to indicate the appropriate cutting point. Moreover, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

We claim:

1. A medical apparatus comprising:
   a catheter head having a large-lumen fitting and a small-lumen fitting;
   a catheter attachable to the catheter head including a large lumen, a small lumen adjacent to the large lumen, a top portion, a bottom portion, and a balloon in communication with the small lumen; and
   a guide tube having a distal end and proximal end attached to the top portion of the catheter at the proximal end.

2. The medical apparatus of claim 1 wherein the catheter head further comprises a first, a second, and a third port and a first and a second port cap operably associated with the first and second ports.

3. The medical apparatus of claim 2 further comprising a valve disposed in the third port.

4. The medical apparatus of claim 1 further comprising a guidewire.

5. The medical apparatus of claim 1 wherein the large-lumen fitting of the catheter head has a flat edge for interconnection with a flat surface of the large lumen of the catheter.

6. The medical apparatus of claim 1 wherein the large-lumen fitting of the catheter head is generally frusto-conical in shape for easy push insertion into the large lumen.

7. The medical apparatus of claim 1 wherein the catheter bears a position mark 2 cm from the bottom end.

8. The medical apparatus of claim 1 further comprising a ridge located on the bottom end portion of the catheter with a diameter at least 1 mm wider than the diameter of the catheter.

9. The medical apparatus of claim 1 wherein the distal end of the guide tube has a diameter wider than the diameter of the catheter.

10. The medical apparatus of claim 1 further comprising a seal sleeve with an interior diameter greater than the diameter of the catheter.

11. The medical apparatus of claim 1 further comprising a flange with a center opening greater than the diameter of the catheter.

12. A feeding tube device comprising:
    a double-lumen catheter having a balloon, a small lumen for inflating the balloon in connection with a bottom portion of the double-lumen catheter and a large lumen for enteral feeding of a patient;
    a guide tube attached to a top portion of the double-lumen catheter and having a tapered proximal end, wherein the guide tube-catheter assembly presents an overall profile substantially no wider than the catheter; and
    a catheter head having a large-lumen fitting and a small-lumen fitting for removably connecting the catheter head to the large lumen and small lumen of the catheter.

13. The feeding tube device of claim 12 wherein the large-lumen fitting has a raised outer lip which causes a friction fit with the large lumen for ease of insertion but more difficult removal.

14. The feeding tube device of claim 12 wherein the double-lumen catheter bears a mark at its distal end for indicating when the catheter has been pushed far enough into position.

15. The feeding tube device of claim 12 further comprising a ridge located on the bottom end of the double-lumen catheter that prevents accidental removal of the catheter by requiring a tug for removal.

16. The feeding tube device of claim 12 wherein the distal end of the guide tube has a diameter wider than the diameter of the double-lumen catheter to ease passage of the catheter; and wherein the guide tube is removable from the double-lumen catheter.

17. The feeding tube device of claim 12 further comprising a catheter seal sleeve with an interior diameter greater than the diameter of the double-lumen catheter for sealing the connection between the catheter and the catheter head.

18. The device of claim 1, wherein the catheter is configured and dimensioned to fit down a throat and into a stomach of a neonate.

19. A feeding tube device for a patient comprising:

a double-lumen catheter including a catheter balloon;

a guide tube removably connected with the double lumen catheter;

a guide wire for guiding the double lumen catheter and guide tube down the throat of a patient;

a catheter head for connecting to the double lumen catheter after removal of the guide tube and guide wire; and a sleeve for sealing the connection between the catheter to the catheter head;

wherein the catheter head includes a feeding port, a medication port, and a balloon filling port;

wherein the feeding port and medication port are in fluid communication with the large lumen of the catheter for simultaneous introduction of medication and nutrition and the balloon filling port is in fluid communication with the small lumen of the catheter for filling the catheter balloon to secure the catheter in place along the patient's stomach wall; and wherein the catheter further includes a position mark and a ridge to better position the catheter in the patient'stomach.

20. The device of claim 19, further comprising a metal lumen fitting connected to the catheter head and coated with plastic to increase surface friction and better secure the connection between the catheter lumen and the catheter head.

* * * * *